United States Patent [19]

Krüger et al.

[11] Patent Number: 5,686,634

[45] Date of Patent: Nov. 11, 1997

[54] PROCESS FOR PRODUCING 5-HYDROXY-6-DEMETHYL-6-DESOXY-6-METHYLENE-11A-CHLOROTETRACYCLINE

[75] Inventors: Wolfgang Krüger; Gisela Krüger, both of Glindenberg, Germany

[73] Assignee: Pfizer, Inc., New York, N.Y.

[21] Appl. No.: 270,639

[22] Filed: Jul. 1, 1994

[51] Int. Cl.[6] .................................. C07C 237/26
[52] U.S. Cl. ........................................... 552/204
[58] Field of Search ................................. 552/204

[56] References Cited

U.S. PATENT DOCUMENTS

| 2,984,686 | 5/1961 | Blackwood | 552/204 |
| 3,026,354 | 3/1962 | Blackwood | 552/204 |
| 4,659,515 | 4/1987 | Lugosi et al. | 552/204 |

OTHER PUBLICATIONS

CA 115:158758 Krueger et al. DD28951945, 1991.

CA 120:323093 Krueger et al, DE4221855A, Jan. 5, 1994.

*Primary Examiner*—Rebecca Cook
*Attorney, Agent, or Firm*—Peter C. Richardson; Paul H. Ginsburg; Seymour G. Bekelnitzky

[57] ABSTRACT

In a process for dehydrating 5-hydroxy-11a-chlorotetracycline-6,12-hemiketal to 5-hydroxy-6-demethyl-6-desoxy-6-methylene-11a-chlorotetracycline, utilizing an acid which is not decomposable by water, formic acid serves as a solvent free from chlorinated hydrocarbons.

7 Claims, No Drawings

PROCESS FOR PRODUCING 5-HYDROXY-6-DEMETHYL-6-DESOXY-6-METHYLENE-11A-CHLOROTETRACYCLINE

FIELD OF THE INVENTION

Our present invention relates to a method of producing 5-hydroxy-6-demethyl-6-desoxy-6-methylene-11a-chlorotetracycline and, more particularly, to a method of dehydrating 5-hydroxy-11a-chlorotetracycline-6,12-hemiketal to 5-hydroxy-6-demethyl-6-desoxy-6-methylene-11a-chlorotetracycline with an acid which is not decomposable by water.

BACKGROUND OF THE INVENTION 5-hydroxy-11a-chlorotetracycline-6,12-hemiketal, hereinafter referred to occasionally as chlorohemiketal, is known and is an intermediate in the synthesis of doxycycline, the most important tetracycline antibiotic.

In the past, for the dehydration of the chlorohemiketal to the 5-hydroxy-6-demethyl-6-desoxy-6-methylene-11a-chlorotetracycline, dehydrating agents were used which included water-free hydrogen fluoride, sulfuric acid, phosphoric acid, perchloric acid, chlorosulfonic acid and thionyl chloride sulfuric acid, the latter two in solution in mixtures of chlorinated hydrocarbons and formic acid (see U.S. Pat. No. 2,984,686, U.S. Pat. No. 3,026,354, German Open Application De-OS 2,216,459, East German Pat. Document DD 219 186 and East German Pat. Document DD 289 519).

Economical results were obtained only with the water-free hydrogen fluoride, with chlorosulfonic acid or sulfuric acid/thionylchloride in formic acid mixtures containing chlorinated hydrocarbons.

With the other known acids only small quantities of a highly impure reaction product was obtainable. Thus the economical system utilized chemicals which were significant environmental pollutants like hydrogen fluoride or substances which were considered carcinogenic like chlorinated hydrocarbons.

The process of DD 219 186 required for the production of 6-demethyl-6-desoxy-6-methylene-5-oxytetracycline and its 11 a chloro derivatives, a water-free formic acid which was not readily accessible and had low stability.

OBJECTS OF THE INVENTION

It is, therefore, the principal object of the present invention to provide an improved method of preparing 5-hydroxy-6-demethyl-6-desoxy-6-methylene-11a-chlorotetracycline or of dehydrating 5-hydroxy-11a-chlorotetracycline-6,12-hemiketal to form 5-hydroxy-6-demethyl-6-desoxy-6-methylene-11a-chlorotetracycline which avoids the drawbacks of the earlier methods.

Another object of the invention is to provide a process which can transform the chlorohemiketal to the 11a-chlorometacycline in high yield and high quality with simultaneous reduction of the danger to the health of personnel and environment.

DESCRIPTION OF THE INVENTION

These objects are attained, in accordance with the invention by utilizing formic acid as the solvent, i.e. as a solvent free from chlorinated hydrocarbons and, particularly, the exclusive solvent for the dehydration.

It has been found, surprisingly, that those acids referred to above which do not decompose by reaction with water and as to which only reduced yields of a highly impure 11a-chlorometacycline have been obtained heretofore, give excellent results when the dehydration is effected in a solution in which formic acid is the sole solvent.

The method of the invention can thus comprise the steps of:

dehydrating 5-hydroxy-11a-chlorotetracycline-6,12hemiketal to 5-hydroxy-6-demethyl-6-desoxy-6-methylene-11a-chlorotetracycline with an acid not decomposable by water in solution in formic acid as an exclusive solvent for said solution; and recovering 5-hydroxy-6-demethyl-6-desoxy-6-methylene11a-chlorotetracycline from said solution.

Preferably the invention is carried out used as a dehydrating solution, a solution of sulfuric acid in formic acid. This has significant cost advantages and minimizes the environmental hazard because of the choice of the acid which is not decomposable by water.

According to a feature of the invention, the dehydrating solution is so prepared, considering the water content of the starting material, that at the end of the reaction in the reaction mixture there is 0–3 moles of water, preferably 1–2 moles of water, per mole of the 5-hydroxy-11a-chlorotetracycline-6,12-hemiketal introduced.

This is indeed surprising because, by contrast with the processes known from DD 219 186 and DD 289 519, no substances which chemically react with water, like chlorosulfonic acid or thionylchloride are required to bind the water. Even the presence of up to 2 moles of water per mole of the chlorohemiketal in the reaction mixture prior to the dehydration or up to 3 moles of water following the dehydration reaction allows excellent results to be obtained in the dehydration.

The preparation of the dehydrating solution can be effected either by dissolving the acid in formic acid having a low water content or by dissolving the acid in formic acid having a higher water content and removing the excess water by adding to the solution a compound chemically reacting with water and which does not yield detrimental reaction products.

For the removal of any excess water, we may use acid anhydrides and acid halogenides, preferably of the dehydrating acid, for example sulfur trioxide (especially in the form of fuming sulfuric acid), thionylchloride and chlorosulfonic acid as especially suitable reagents.

The ratio of chlorohemiketal: formic acid: dehydrating acid in the reaction mixture can be in the range of 1:10–20:5–20. Especially preferred are proportions in the range of 1:15–17:8–17.

When starting materials having a high water content are used, the amount of the water binding agent must be so calculated that after the conclusion of the reaction, not more than 3 moles of water per mole of chlorohemiketal introduced, will be present. Optimum results are achieved with 1–2 moles of water. A lesser water content in the reaction mixture is permissible, but does not have any advantages.

The chlorohemiketal can be used as the base, or its hydrochloride, or as some other salt and the removal of any optionally present excess water can be effected prior to or after the chlorohemiketal addition. Preferably, however, a prior dewatering of the dehydrating mixture by addition of the dewatering agent to the prepared formic acid or formic acid dehydrating acid mixture at a temperature between −30 and +30° C., depending upon the dewatering agent used, is employed.

The dehydration of the chlorohemiketal can be effected by introducing it into the acid mixture with a reaction time of 2 to 6 hours at a temperature of −10° C. to +30° C., the lower temperature being preferred at the beginning of the reaction and higher temperatures within this range being preferred toward the end of the reaction.

The isolation of the reaction product is effected in a known manner by precipitation of low solubility solids, for example the toluene sulfonate salt of the desired product.

SPECIFIC EXAMPLES

Example 1

150 ml formic acid (water content 165 g/l=1.375 mole $H_2O$)

88 ml 96% sulfuric acid (=0.36 mole $H_2O$)

127 g 11a-chlorohemiketal-hydrochloride 79.9%=0.191 mole (contains 13.6% NaCl and 6.5% $H_2O$=0.46 mole.

140 ml thionylchloride (=229.3 g=1.93 mole)

Water content of the mixture at the conclusion of the reaction=1.375+0.36+0.46+0.191−1.93=0.456 mole (corresponding to 2.39 mole water per 1 mole chlorohemiketal).

The sulfuric acid is added dropwise at 10° to 20° C. with stirring to the formic acid and then, without further cooling, the thionylchloride is added, generating hydrogen chloride and sulfur dioxide by reaction with water, the temperature dropping to −25° C. The solution is stirred for an hour and then has a temperature of about −10° C. The chlorohemiketal is combined with this solution over a period of 40 minutes and the mixture is then stirred for an additional 4 hours, the temperature being permitted to rise to room temperature.

The mixture is then cooled and at a temperature of 10° to 15° C., 400 ml of isopropanol is added. The solution is filtered and combined under strong stirring with a solution of 115 g p-toluene sulfonic acid in 900 ml isopropanol and 400 ml acetone.

The resulting mixture is sealed with 0.2 g 11a-chlorometacycline-p-toluene sulfonate and stirred until crystallization commences. The solution is allowed to stand. The crystals are separated on a suction filter, washed with acetone and dried.

222.7 g of 11a-chlorometacycline-p-toluene sulfonate with a purity of 99% is obtained in a yield of 88% of theoretical.

Example 2

Example 1 is repeated with 106 g of the chlorohemiketal base dihydrate (=0.2 moles with 0.38 mole water). The yield of the 11a-chlorometacycline toluene sulfonate is 86.2% of the theoretical.

Example 3

140 ml formic acid (water content 25 g/l=3.5 g equals 0.2 mole water).

90 ml sulfuric acid (96%=6.6 g=0.37 mole water)

107.5 g chlorohemiketal hydrochloride (99% 0.01 g/$H_2O$/g =1.1 g=0.06 mole water.

41 ml thionylchloride (67 g=0.56 mole).

The sulfuric acid is added dropwise with cooling to the formic acid and then, without further cooling, the thionyl-chloride is added. After stirring for 1 hour the mixture at a temperature of about −10° C. is combined with the chlorohemiketal. Upon stirring for 4 hours the temperature rises to 22° C. After dilution with isopropanol and precipitation with toluene sulfonic acid, the 11a-chlorometacycline is precipitated as the toluene sulfonate in a yield of 91.5% of theoretical.

Example 4

150 ml formic acid (water content 165 g/l=1.375 moles water) 97.2 ml of fuming sulfuric acid is added with stirring and cooling in the range of −5° C. to +5° C., in a dropwise manner. The fuming sulfuric acid contains 65% $SO_3$(=1.576 moles).

In the thus prepared dehydrating mixture at −10°—5° C., 132 g (0.2 moles) of chlorohemiketal hydrochloride (79.9%, water content 65%=0.477 moles) is introduced. The mixture is stirred for 5 hours and the temperature is permitted to rise to 23° C. It is diluted as is customary with isopropanol and the product is crystallized and filtered from the solution as the toluene sulfonate which is obtained in a yield of 87.9% of theoretical.

Example 5

150 ml formic acid (0.025 g water/ml=0.21 mole)

100 ml trifluoroacetic acid 107.5 g chlorohemiketal (0.2 mole, 0.01 g water/g=0.06 mole)

16.9 ml fuming sulfuric acid with 65% $SO_3$ (0.27 mole)

The fuming sulfuric acid is added dropwise under cooling to a mixture of the formic acid with the trifluoroacetic acid and the chlorohemiketal is introduced into the thus prepared dehydrating solution. The process was continued in accordance with Example 4. Chlorometacycline toluene sulfonate was obtained in 92% of theoretical.

We claim:

1. A process for the preparation of 5-hydroxy-6-demethyl-6-desoxy-6-methylene-11a-chlorotetracycline which comprises treating 5-hydroxy-11a-chlorotetracycline-6,12hemiketal, in the absence of a diluent or any material which will react with water, with a dehydrating solution consisting of sulfuric acid, as dehydrating agent, and formic acid, as solvent.

2. The process of claim 1 wherein the reaction mixture further consists of an amount of water, prior to the dehydration, which will yield a solution, after dehydration, containing 0 to 3 moles of water per mole of hemiketal.

3. The process of claim 2 wherein said water is provided with said hemiketal, formic acid, sulfuric acid or any combination thereof.

4. The process of claim 2 wherein excess water in the dehydrating solution is removed by treatment with at least one compound capable of reacting with said water.

5. The process of claim 4 wherein said compound capable of reacting with said water is selected from the group consisting of $SO_3$, fuming sulfuric acid, chlorosulfonic acid and thionyl chloride.

6. The process of claim 5 wherein said compound capable of reacting with said water is $SO_3$.

7. The process of claim 5 wherein said compound capable of reacting with said water is fuming sulfuric acid.

* * * * *